US012558431B2

(12) United States Patent
Shin et al.

(10) Patent No.: US 12,558,431 B2
(45) Date of Patent: Feb. 24, 2026

(54) METHOD OF PREPARING PROTEIN CONJUGATE

(71) Applicant: HANMI PHARM. CO., LTD, Hwaseong-si (KR)

(72) Inventors: Cheongbyeol Shin, Hwaseong-si (KR); Dooseo Jang, Hwaseong-si (KR); Ji Hye Moon, Hwaseong-si (KR); Dong Hyun Kim, Hwaseong-si (KR); Ji Eun Lee, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 1075 days.

(21) Appl. No.: 17/627,913

(22) PCT Filed: Jul. 18, 2019

(86) PCT No.: PCT/KR2019/008911

§ 371 (c)(1),
(2) Date: Jan. 18, 2022

(87) PCT Pub. No.: WO2021/010531

PCT Pub. Date: Jan. 21, 2021

(65) Prior Publication Data

US 2022/0273808 A1 Sep. 1, 2022

(51) Int. Cl.

| | |
|---|---|
| ***A61K 47/68*** | (2017.01) |
| ***A61K 47/60*** | (2017.01) |
| ***C07K 14/605*** | (2006.01) |
| ***C08G 65/325*** | (2006.01) |
| *A61K 38/00* | (2006.01) |

(52) U.S. Cl.

CPC .............. *A61K 47/68* (2017.08); *A61K 47/60* (2017.08); *C07K 14/605* (2013.01); *C08G 65/325* (2013.01); *A61K 38/00* (2013.01)

(58) Field of Classification Search

None

See application file for complete search history.

(56) References Cited

U.S. PATENT DOCUMENTS

| | | | | |
|---|---|---|---|---|
| 9,394,546 B2 | 7/2016 | Kim et al. | | |
| 11,717,577 B2 * | 8/2023 | Shin | ....................... | A61K 38/00 424/178.1 |

FOREIGN PATENT DOCUMENTS

| | | | |
|---|---|---|---|
| KR | 10-2014-0109342 A | | 9/2014 |
| KR | 10-2016-0032699 A | | 3/2016 |
| KR | 10-2017-0104409 A | | 9/2017 |
| KR | 10-2018-0071241 A | | 6/2018 |
| WO | 96/32478 | A1 | 10/1996 |
| WO | 97/34631 | A1 | 9/1997 |
| WO | 2017/146443 | A1 | 8/2017 |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Guido et al (Curr Med Chem. 2008;15(1):37-46) (Year: 2008).*
Clark et al (J. Med. Chem., 2014, 57 (12), pp. 5023-5038) (Year: 2014).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Vajdos et al. (J Mol Biol. Jul. 5, 2002;320(2):415-28) (Year: 2002).*
Brown et al. (J Immunol. May 1996;156(9):3285-91) (Year: 1996).*
Vattekatte, (PeerJ. Mar. 6, 2020:8:e8408. (Year: 2020).*
Edwards et al. (Mol Biol. Nov. 14, 2003;334(1):103-18) (Year: 2003).*
Lloyd et al. (Protein Eng Des Sel. Mar. 2009;22(3):159-68. Epub Oct. 29, 2008.) (Year: 2009).*
Goel et al. (J Immunol. Dec. 15, 2004;173(12):7358-67) (Year: 2004).*
Khan et al. (J Immunol (2014) 192 (11): 5398-5405) (Year: 2014).*
Poosarla et al. (Biotechnol Bioeng. Jun. 2017 ; 114(6): 1331-1342) (Year: 2017).*
Rabia, et al. (Biochem Eng J. Sep. 15, 2018:137:365-374. Epub Jun. 5, 2018) (Year: 2018).*
WHO Drug Information, 2018, 212 pgs., vol. 32, No. 2, <https://apps.who.int/medicinedocs/documents/s23502en/s23502en.pdf>.
International Search Report for PCT/KR2019/008911 dated, Apr. 17, 2020 (PCT/ISA/210).

* cited by examiner

*Primary Examiner* — Brian Gangle
*Assistant Examiner* — Andrea K Mccollum
(74) *Attorney, Agent, or Firm* — Sughrue Mion, PLLC

(57) ABSTRACT

A method of preparing a protein conjugate contains linking a mono-PEGylated immunoglobulin Fc region to a dual agonist exhibiting activity on both glucagon-like peptide-1 (GLP-1) and glucagon. The mono-PEGylated immunoglobulin Fc region is prepared by linking a linker of Formula 1 to the N-terminus of an immunoglobulin Fc region comprising a hinge sequence:

$CHO\text{-}L1\text{-}(OCH_2CH_2)_nO\text{-}L2\text{-}R$ [Formula 1].

13 Claims, 2 Drawing Sheets

Specification includes a Sequence Listing.

SEQUENCE LISTING

```
<160> NUMBER OF SEQ ID NOS: 25

<210> SEQ ID NO 1
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16)..(20)
<223> OTHER INFORMATION: amino acids at position 16 and position 20 form
      a ring

<400> SEQUENCE: 1

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 2
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid

<400> SEQUENCE: 2

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid

<400> SEQUENCE: 3

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 4
<211> LENGTH: 12
<212> TYPE: PRT
```

<213> ORGANISM: Homo sapiens

<400> SEQUENCE: 4

Glu Ser Lys Tyr Gly Pro Pro Cys Pro Ser Cys Pro
1 5 10

<210> SEQ ID NO 5
<211> LENGTH: 3
<212> TYPE: PRT
<213> ORGANISM: Artificial Sequence
<220> FEATURE:
<223> OTHER INFORMATION: Variant of hinge region

<400> SEQUENCE: 5

Ser Cys Pro
1

<210> SEQ ID NO 6
<211> LENGTH: 4
<212> TYPE: PRT
<213> ORGANISM: Artificial Sequence
<220> FEATURE:
<223> OTHER INFORMATION: Variant of hinge region

<400> SEQUENCE: 6

Pro Ser Cys Pro
1

<210> SEQ ID NO 7
<211> LENGTH: 221
<212> TYPE: PRT
<213> ORGANISM: Homo sapiens

<400> SEQUENCE: 7

Pro Ser Cys Pro Ala Pro Glu Phe Leu Gly Gly Pro Ser Val Phe Leu
1 5 10 15

Phe Pro Pro Lys Pro Lys Asp Thr Leu Met Ile Ser Arg Thr Pro Glu
20 25 30

Val Thr Cys Val Val Val Asp Val Ser Gln Glu Asp Pro Glu Val Gln
35 40 45

Phe Asn Trp Tyr Val Asp Gly Val Glu Val His Asn Ala Lys Thr Lys
50 55 60

Pro Arg Glu Glu Gln Phe Asn Ser Thr Tyr Arg Val Val Ser Val Leu
65 70 75 80

Thr Val Leu His Gln Asp Trp Leu Asn Gly Lys Glu Tyr Lys Cys Lys
85 90 95

Val Ser Asn Lys Gly Leu Pro Ser Ser Ile Glu Lys Thr Ile Ser Lys
100 105 110

Ala Lys Gly Gln Pro Arg Glu Pro Gln Val Tyr Thr Leu Pro Pro Ser
115 120 125

Gln Glu Glu Met Thr Lys Asn Gln Val Ser Leu Thr Cys Leu Val Lys
130 135 140

Gly Phe Tyr Pro Ser Asp Ile Ala Val Glu Trp Glu Ser Asn Gly Gln
145 150 155 160

Pro Glu Asn Asn Tyr Lys Thr Thr Pro Pro Val Leu Asp Ser Asp Gly
165 170 175

Ser Phe Phe Leu Tyr Ser Arg Leu Thr Val Asp Lys Ser Arg Trp Gln
180 185 190

Glu Gly Asn Val Phe Ser Cys Ser Val Met His Glu Ala Leu His Asn
195 200 205

-continued

```
His Tyr Thr Gln Lys Ser Leu Ser Leu Ser Leu Gly Lys
    210                 215                 220


<210> SEQ ID NO 8
<211> LENGTH: 11
<212> TYPE: PRT
<213> ORGANISM: Artificial Sequence
<220> FEATURE:
<223> OTHER INFORMATION: Variant of hinge region

<400> SEQUENCE: 8

Glu Ser Lys Tyr Gly Pro Pro Pro Ser Cys Pro
1               5                   10


<210> SEQ ID NO 9
<211> LENGTH: 11
<212> TYPE: PRT
<213> ORGANISM: Artificial Sequence
<220> FEATURE:
<223> OTHER INFORMATION: Variant of hinge region

<400> SEQUENCE: 9

Glu Ser Lys Tyr Gly Pro Pro Cys Pro Ser Pro
1               5                   10


<210> SEQ ID NO 10
<211> LENGTH: 10
<212> TYPE: PRT
<213> ORGANISM: Artificial Sequence
<220> FEATURE:
<223> OTHER INFORMATION: Variant of hinge region

<400> SEQUENCE: 10

Glu Ser Lys Tyr Gly Pro Pro Cys Pro Ser
1               5                   10


<210> SEQ ID NO 11
<211> LENGTH: 10
<212> TYPE: PRT
<213> ORGANISM: Artificial Sequence
<220> FEATURE:
<223> OTHER INFORMATION: Variant of hinge region

<400> SEQUENCE: 11

Glu Ser Lys Tyr Gly Pro Pro Cys Pro Pro
1               5                   10


<210> SEQ ID NO 12
<211> LENGTH: 8
<212> TYPE: PRT
<213> ORGANISM: Artificial Sequence
<220> FEATURE:
<223> OTHER INFORMATION: Variant of hinge region

<400> SEQUENCE: 12

Lys Tyr Gly Pro Pro Cys Pro Ser
1               5


<210> SEQ ID NO 13
<211> LENGTH: 8
<212> TYPE: PRT
<213> ORGANISM: Artificial Sequence
<220> FEATURE:
<223> OTHER INFORMATION: Variant of hinge region

<400> SEQUENCE: 13
```

-continued

```
Glu Ser Lys Tyr Gly Pro Pro Cys
1               5


<210> SEQ ID NO 14
<211> LENGTH: 7
<212> TYPE: PRT
<213> ORGANISM: Artificial Sequence
<220> FEATURE:
<223> OTHER INFORMATION: Variant of hinge region

<400> SEQUENCE: 14

Glu Lys Tyr Gly Pro Pro Cys
1               5


<210> SEQ ID NO 15
<211> LENGTH: 6
<212> TYPE: PRT
<213> ORGANISM: Artificial Sequence
<220> FEATURE:
<223> OTHER INFORMATION: Variant of hinge region

<400> SEQUENCE: 15

Glu Ser Pro Ser Cys Pro
1               5


<210> SEQ ID NO 16
<211> LENGTH: 5
<212> TYPE: PRT
<213> ORGANISM: Artificial Sequence
<220> FEATURE:
<223> OTHER INFORMATION: Variant of hinge region

<400> SEQUENCE: 16

Glu Pro Ser Cys Pro
1               5


<210> SEQ ID NO 17
<211> LENGTH: 4
<212> TYPE: PRT
<213> ORGANISM: Artificial Sequence
<220> FEATURE:
<223> OTHER INFORMATION: Variant of hinge region

<400> SEQUENCE: 17

Pro Ser Cys Pro
1


<210> SEQ ID NO 18
<211> LENGTH: 10
<212> TYPE: PRT
<213> ORGANISM: Artificial Sequence
<220> FEATURE:
<223> OTHER INFORMATION: Variant of hinge region

<400> SEQUENCE: 18

Glu Ser Lys Tyr Gly Pro Pro Ser Cys Pro
1               5                   10


<210> SEQ ID NO 19
<211> LENGTH: 9
<212> TYPE: PRT
<213> ORGANISM: Artificial Sequence
<220> FEATURE:
<223> OTHER INFORMATION: Variant of hinge region

<400> SEQUENCE: 19

Lys Tyr Gly Pro Pro Pro Ser Cys Pro
```

1 5

<210> SEQ ID NO 20
<211> LENGTH: 9
<212> TYPE: PRT
<213> ORGANISM: Artificial Sequence
<220> FEATURE:
<223> OTHER INFORMATION: Variant of hinge region

<400> SEQUENCE: 20

Glu Ser Lys Tyr Gly Pro Ser Cys Pro
1 5

<210> SEQ ID NO 21
<211> LENGTH: 8
<212> TYPE: PRT
<213> ORGANISM: Artificial Sequence
<220> FEATURE:
<223> OTHER INFORMATION: Variant of hinge region

<400> SEQUENCE: 21

Glu Ser Lys Tyr Gly Pro Pro Cys
1 5

<210> SEQ ID NO 22
<211> LENGTH: 7
<212> TYPE: PRT
<213> ORGANISM: Artificial Sequence
<220> FEATURE:
<223> OTHER INFORMATION: Variant of hinge region

<400> SEQUENCE: 22

Lys Tyr Gly Pro Pro Cys Pro
1 5

<210> SEQ ID NO 23
<211> LENGTH: 7
<212> TYPE: PRT
<213> ORGANISM: Artificial Sequence
<220> FEATURE:
<223> OTHER INFORMATION: Variant of hinge region

<400> SEQUENCE: 23

Glu Ser Lys Pro Ser Cys Pro
1 5

<210> SEQ ID NO 24
<211> LENGTH: 6
<212> TYPE: PRT
<213> ORGANISM: Artificial Sequence
<220> FEATURE:
<223> OTHER INFORMATION: Variant of hinge region

<400> SEQUENCE: 24

Glu Ser Pro Ser Cys Pro
1 5

<210> SEQ ID NO 25
<211> LENGTH: 4
<212> TYPE: PRT
<213> ORGANISM: Artificial Sequence
<220> FEATURE:
<223> OTHER INFORMATION: Variant of hinge region -continued

```
<400> SEQUENCE: 25

Glu Pro Ser Cys
1
```

METHOD OF PREPARING PROTEIN CONJUGATE

CROSS REFERENCE TO RELATED APPLICATIONS

This application is a National Stage of International Application No. PCT/KR2019/008911 filed Jul. 18, 2019.

SEQUENCE LISTING

The content of the electronically submitted sequence listing, file name: Q271756 sequence listing as filed.txt; size: 7.4 KB; and date of creation: Jul. 24, 2025, filed herewith, is incorporated herein by reference in its entirety.

TECHNICAL FIELD

The present invention relates to a method for preparing a protein conjugate.

BACKGROUND ART

Physiologically active polypeptides are easily denatured due to low stability, degraded by proteases in the blood, and easily removed by the kidneys or liver. Thus, in order to maintain blood concentration and titer of a protein drug containing a physiologically active polypeptide as a pharmacological component, the protein drug needs to be frequently administered to a patient. However, since most protein drugs are administered to patients in the form of an injection, frequent administration via injection to maintain blood concentration of the physiologically active polypeptide causes severe pain to the patients and increases costs for treatment. To solve these problems, efforts have been made to maximize the efficacy of protein drugs by increasing blood stability of the protein drugs and maintaining the blood concentration thereof at a high level for a long period of time. However, these long-acting formulations of protein drugs should increase the stability of the protein drugs and maintain the titer of the drug at a sufficiently high level while not inducing immune responses in patients.

As a method of stabilizing proteins, inhibiting contact with proteases, and suppressing renal clearance, a method of chemically adding a highly soluble polymer such as polyethylene glycol (hereinafter referred to as "PEG") to the surfaces of protein drugs has been conventionally used. However, while the method of using PEG may extend in vivo duration of the peptide drug by increasing a molecular weight of PEG, the titer of the peptide drug significantly decreases as the molecular weight increases, and a yield may decrease due to low reactivity with the peptide.

Therefore, as a method for increasing serum half-life, a conjugate of an immunoglobulin fragment and a physiologically active polypeptide has been used, and various studies have been conducted to improve a preparation method therefor (Korean Patent Application Laid-open Publication No. 10-2014-0109342).

Meanwhile, oxyntomodulin is an example of a dual agonist exhibiting activity on both GLP-1 and glucagon and is produced from pre-glucagon as a precursor. As a peptide having dual function of binding to both glucagon-like peptide-1 (GLP-1) and glucagon receptors as a main property, research has been conducted into oxyntomodulin for various purposes such as for the treatment of obesity, diabetes, hyperlipidemia, fatty liver, and the like.

However, oxyntomodulin has a short in vivo half-life and activity thereof is not sufficient for the treatment of obesity, diabetes, hyperlipidemia, fatty liver, and the like, causing a problem of high-dose administration. Therefore, there is a need for research and development to prepare oxyntomodulin with an increased half-life.

DISCLOSURE

Technical Problem

An object of the present invention is to provide a method for preparing a protein conjugate.

Another object of the present invention is to provide a protein conjugate prepared by way of the method.

Technical Solution

One aspect of the present invention provides a novel method for preparing a protein conjugate.

In an embodiment, the present invention provides a method for preparing a protein conjugate including preparing a conjugate by linking a mono-PEGylated immunoglobulin Fc region, which is prepared by linking a linker of Formula 1 below to the N-terminus of an immunoglobulin Fc region comprising a hinge sequence, to a dual agonist exhibiting activity on both GLP-1 and glucagon:

$$CHO\text{-}L1\text{-}(OCH_2CH_2)_nO\text{-}L2\text{-}R \quad \text{[Formula 1]}$$

wherein in Formula 1:

L1 is a straight- or branched-chain $C_1$-$C_6$ alkylene;

L2 is -a1-CONH—, -a1-NHCO—, -a1-NHCO-a2-, -COO—, -b1-COO—, -COO-b2-, or -b1-COO-b2-, and a1, a2, b1, and b2 are each independently a straight- or branched-chain $C_1$-$C_6$ alkylene;

n is from 10 to 2,400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

In the preparation method according to the previous embodiment, the mono-PEGylated immunoglobulin Fc region may be prepared by linking the linker of Formula 1 above to the N-terminus of the immunoglobulin Fc region at a pH of 4.0 to 8.0 in the presence of a reducing agent.

In the preparation method according to any of the previous embodiments, the conjugate may be prepared by linking the linker of the mono-PEGylated immunoglobulin Fc region to a dual agonist exhibiting activity on both GLP-1 and glucagon at a pH of 5.5 to 8.0.

In the preparation method according to any of the previous embodiments, the preparing of the conjugate may include reacting the mono-PEGylated immunoglobulin Fc region with the dual agonist in a molar ratio of 1:1 to 1:3.

In the preparation method according to any of the previous embodiments, the method may include: preparing a mono-PEGylated immunoglobulin Fc region by linking a linker of Formula 1 above to the N-terminus of an immunoglobulin Fc region; and preparing a conjugate by linking the linker of the mono-PEGylated immunoglobulin Fc region prepared in the step above to a dual agonist exhibiting activity on both GLP-1 and glucagon.

In the preparation method according to any of the previous embodiments, the linker of the mono-PEGylated immunoglobulin Fc region may be linked to a cysteine of the dual agonist.

In the preparation method according to any of the previous embodiments, the method may include: preparing a mono-PEGylated immunoglobulin Fc region by linking a linker of Formula 1 above to the N-terminus of an immunoglobulin Fc region; purifying the mono-PEGylated immunoglobulin Fc region prepared in the step above by anion-exchange chromatography in a buffer solution with a pH of 6.0 to 8.5; and preparing a conjugate by linking the linker of the mono-PEGylated immunoglobulin Fc region purified in the step above to a dual agonist exhibiting activity on both GLP-1 and glucagon.

In the preparation method according to any of the previous embodiments, the method may be performed without ultrafiltration/diafiltration after preparing the mono-PEGylated immunoglobulin Fc region.

In the preparation method according to any of the previous embodiments, the method may further include purifying the conjugate by performing hydrophobic interaction chromatography once.

In the preparation method according to any of the previous embodiments, in Formula 1 above, L1 is a straight- or branched-chain $C_1$-$C_6$ alkylene; L2 is -a1-NHCO- or -a1-NHCO-a2-, a1 and a2 are each independently a straight- or branched-chain $C_1$-$0_6$ alkylene; n is from 200 to 250; and R is maleimide.

In the preparation method according to any of the previous embodiments, the linker may have a structure of Formula 2 below:

[Formula 2]

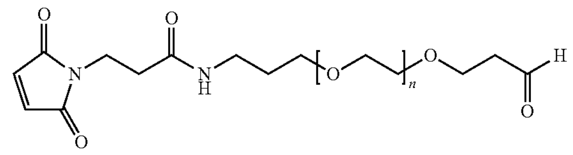

wherein in Formula 2, n is from 200 to 250.

In the preparation method according to an embodiment, the linker may have a size of 1 kDa to 100 kDa.

In the preparation method according to any of the previous embodiments, the mono-PEGylated immunoglobulin Fc region may have a structure of Formula 3 below.

[Formula 3]

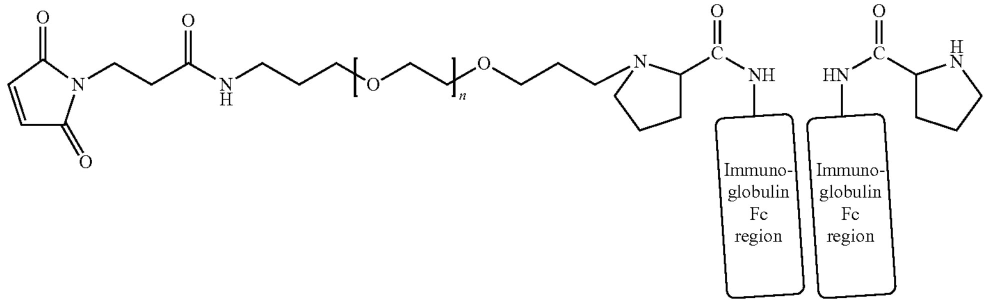

In the preparation method according to any of the previous embodiments, the immunoglobulin Fc region may have an amino acid sequence of SEQ ID NO: 7.

In the preparation method according to any of the previous embodiments, the dual agonist may have one of the amino acid sequences of SEQ ID NOS: 1 to 3.

Another aspect of the present invention provides a protein conjugate prepared by way of the method.

Advantageous Effects

According to the method for preparing a protein conjugate according to the present invention, a protein conjugate may be prepared with a high yield even though some of conventional purification processes are omitted, and thus productivity of the protein conjugate may be increased.

BEST MODE

Figure 1:
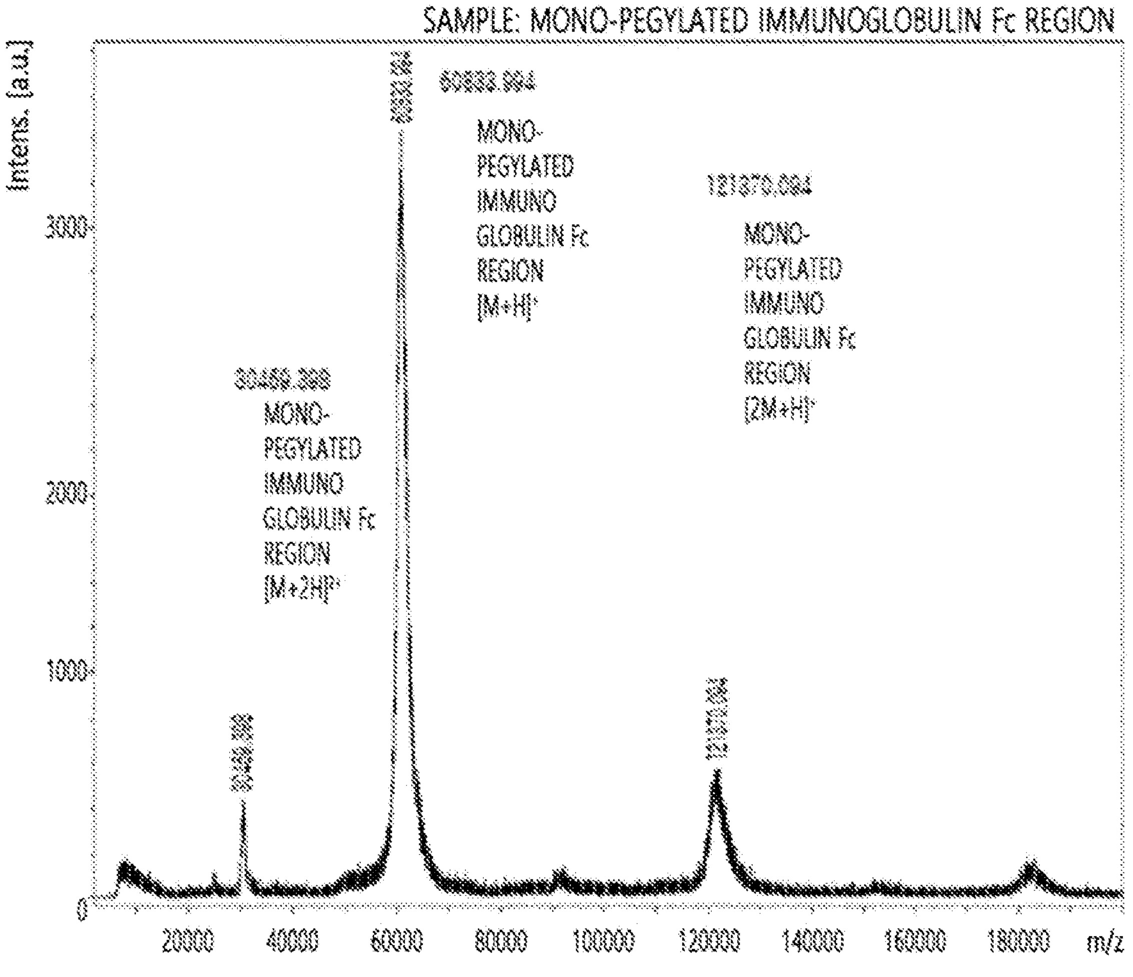
FIG. 1 shows results of analyzing a structure of a mono-PEGylated immunoglobulin Fc region by MALDI-TOF assay.
Figure 2:
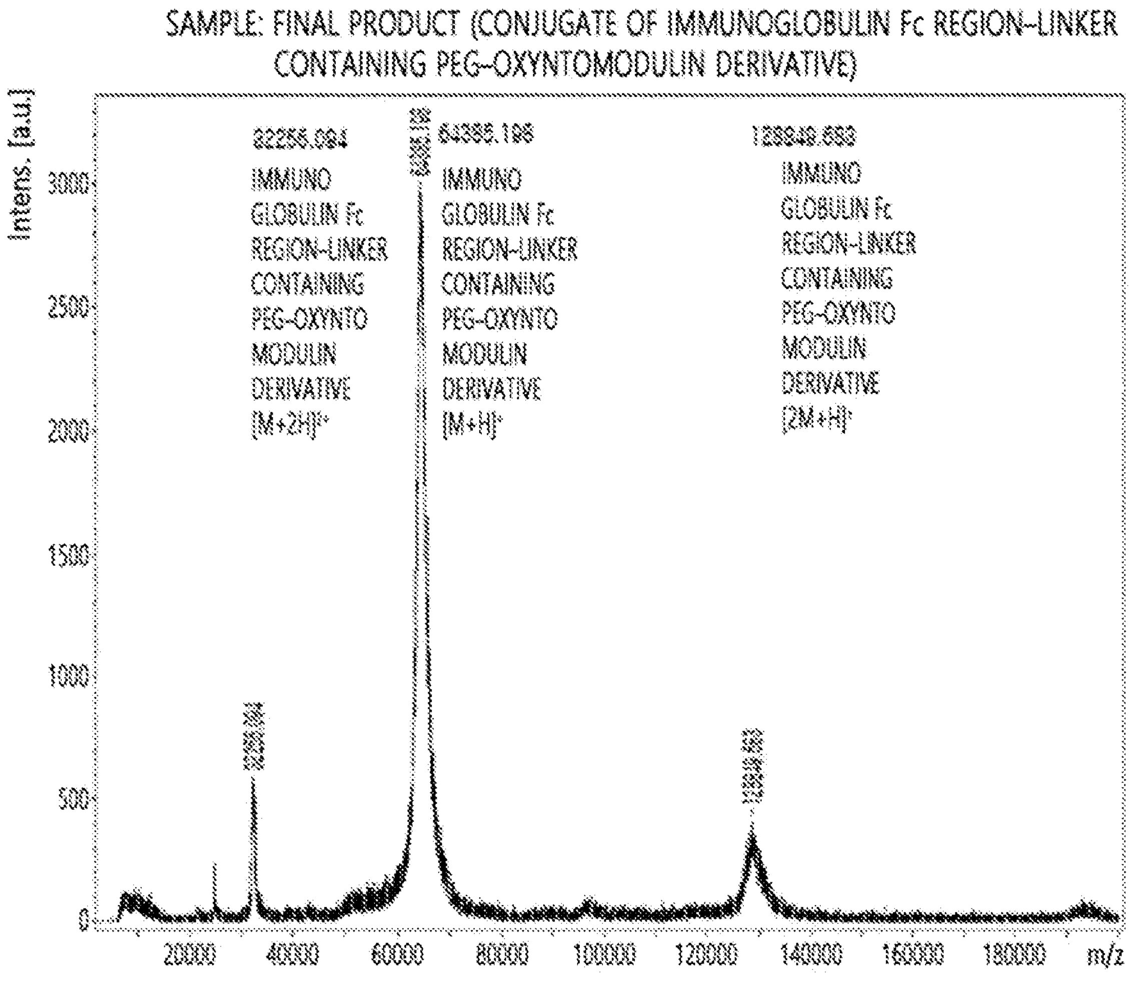
FIG. 2 shows results of analyzing a structure of an immunoglobulin Fc region—linker containing PEG-oxyntomodulin derivative conjugate prepared by way of the method of the present invention.

Hereinafter, embodiments of the present invention will be described in detail.

Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

Also, those skilled in the art will recognize or be able to ascertain, using no more than routine experimentation, many equivalents to specific embodiments of the present invention. Such equivalents are intended to be encompassed in the scope of the following claims.

Throughout the specification, not only the conventional one-letter and three-letter codes for naturally occurring amino acids, but also those three-letter codes generally allowed for other amino acids, such as α-aminoisobutyric acid (Aib), N-methylglycine (Sar), and α-methyl-glutamic acid are used. In addition, the amino acids mentioned herein are abbreviated according to the nomenclature rules of IUPAC-IUB as follows.

| | |
|---|---|
| alanine Ala, A | arginine Arg, R |
| asparagine Asn, N | aspartic acid Asp, D |
| cysteine Cys, C | glutamic acid Glu, E |
| glutamine Gln, Q | glycine Gly, G |
| histidine His, H | isoleucine Ile, I |
| leucine Leu, L | lysine Lys, K |
| methionine Met, M | phenylalanine Phe, F |
| proline Pro, P | serine Ser, S |
| threonine Thr, T | tryptophan Trp, W |
| tyrosine Tyr, Y | valine Val, V |

An aspect of the present invention provides a method for preparing a protein conjugate.

The preparation method of the present invention is a method for preparing a protein conjugate in which a dual agonist is linked to an immunoglobulin Fc region via a linker and is characterized by sequentially performing (i) linking a linker including polyethyleneglycol (PEG) to an immunoglobulin Fc region, and (ii) linking the immunoglobulin Fc region—linked linker to a dual agonist exhibiting activity on both GLP-1 and glucagon. That is, the method is characterized by performing preparation steps in a predetermined order, i.e., after performing a first step of linking the PEG-containing linker to the immunoglobulin Fc region, a second step of linking the dual agonist to the linker, which is linked to the immunoglobulin Fc region, is performed. This preparation method may be referred to as used as "reverse order preparation method" in the disclosure.

In the preparation method according to the present invention in which the PEG-containing linker is first linked to the immunoglobulin Fc region, ultrafiltration/diafiltration and purification by hydrophobic interaction chromatography may be omitted. Although the purification step is omitted, it was confirmed that the protein conjugate may be prepared with a high yield.

According to the convention preparation method in which the linker is first linked to the dual agonist and then linked to the immunoglobulin Fc region, when the dual agonist-linked linker (e.g., polyethylene glycol) is linked to the immunoglobulin Fc region, ultrafiltration/diafiltration is required as a separate process after the linker is linked to the dual agonist and before the linked product is linked to the immunoglobulin Fc region to reduce the risk of aggregation that may occur due to low pH conditions (at about a pH of 3.0) of an equilibrium buffer and an elution buffer used for purification of the dual agonist-linked linker and to adjust the pH conditions for reaction using an appropriate buffer.

On the contrary, in the preparation method according to the present invention in which the linker is first linked to the immunoglobulin Fc region, a pH of a buffer used in purification of the immunoglobulin Fc region—linked linker is relatively high, and thus the ultrafiltration/diafiltration process is omitted and then a process of linking the immunoglobulin Fc region—linked linker to the dual agonist may be performed.

Therefore, in the preparation method of the present invention, ultrafiltration/diafiltration may not be performed after preparing the mono-PEGylated immunoglobulin Fc region, but the present invention is not limited thereto. In the method for preparing a protein conjugate according to the present invention, a pH of a solution used to purify the mono-PEGylated immunoglobulin Fc region is not significantly different from a pH of a solution used for a subsequent reaction so that linkage to the dual agonist may be performed without conducting the ultrafiltration/diafiltration. By omitting the ultrafiltration/diafiltration process, the risk of formation of aggregate impurities in a concentration step may be reduced and the preparation process may be simplified so that cost reduction effects may be expected in the case where the technology is commercialized.

Also, the preparation method of the present invention may further include purifying the conjugate by hydrophobic interaction chromatography, without being limited thereto.

Specifically, the hydrophobic interaction chromatography may be performed only once or more than once in accordance with properties of the dual agonist of the protein conjugate and type and size of the linker.

According to the preparation method of the present invention, not only an amount of the dual agonist that is an expensive drug may be reduced but also an amount of unreacted immunoglobulin Fc regions may be reduced, so that the entire or a part of the purification process by hydrophobic interaction chromatography may be omitted to obtain effects on reducing raw materials required for preparation of the protein conjugate and costs therefor compared to the conventional method.

Meanwhile, although the ultrafiltration/diafiltration and hydrophobic interaction chromatography processes, which have been performed in the conventional method for preparing the protein conjugate, are omitted and only the final purification process (e.g., hydrophobic interaction chromatography once) is performed in the preparation method of the present invention, it is advantageous in that a purity of the final conjugate obtained by the present invention is similar to that of the conventional preparation method. That is, according to the preparation method of the present invention, the final purity may be maintained even though some of the purification processes are omitted so that productivity of the protein conjugate may be improved.

The purity of the protein conjugate according to the present invention may be measured by any method well known in the art and examples thereof may be SE-HPLC, RP-HPLC, and IE-HPLC, without being limited thereto.

According to the preparation method of the present invention, the final purity of the protein conjugate may be 90% or more, specifically, 91%, 92%, 93%, 94%, 95%, 96%, 97%, 98%, or 99% or more, without being limited thereto.

Meanwhile, in the preparation method of the present invention, the mono-PEGylated immunoglobulin Fc region is prepared first and then linked to the dual agonist, so that the protein conjugate may be prepared with a high yield compared to the conventional method in terms of not only the dual agonist but also the immunoglobulin Fc region.

In an embodiment of the present invention, it was confirmed that the yield of the protein conjugate obtained by the preparation method of the present invention was increased twice or more compared to the yield of the protein conjugate obtained by the conventional method.

Specifically, the preparation method of the present invention includes preparing a conjugate by linking a mono-PEGylated immunoglobulin Fc region, which is prepared by linking a linker of Formula 1 below to the N-terminus of an immunoglobulin Fc region including a hinge sequence, to a dual agonist exhibiting activity on both GLP-1 and glucagon:

$$CHO\text{-}L1\text{-}(OCH_2CH_2)_nO\text{-}L2\text{-}R \quad \text{[Formula 1]}$$

In Formula 1 above,

L1 is a straight- or branched-chain $C_1$-$C_6$ alkylene;

L2 is -a1-CONH—, -a1-NHCO—, -a1-NHCO-a2-, -COO—, -b1-COO-—, -COO-b2-, or -b1-COO-b2-, and a1, a2, b1, and b2 are each independently a straight- or branched-chain $C_1$-$C_6$ alkylene;

n is from 10 to 2,400;

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof, without being limited thereto.

More specifically, the preparation method may include: preparing a mono-PEGylated immunoglobulin Fc region by linking a linker of Formula 1 above to the N-terminus of an immunoglobulin Fc region; and preparing a conjugate by linking the linker of the mono-PEGylated immunoglobulin Fc region prepared in the above-described step to a dual agonist exhibiting activity on both GLP-1 and glucagon, or the preparation method may include: preparing a mono-PEGylated immunoglobulin Fc region by linking a linker of Formula 1 to the N-terminus of an immunoglobulin Fc region; purifying the mono-PEGylated immunoglobulin Fc region prepared in the above-described step by anion-exchange chromatography in a buffer solution with a pH of 6.0 to 8.5, a pH of 6.0 to 8.0, a pH of 6.0 to 7.5, a pH of 6.0 to 7.0, a pH of 6.1 to 6.9, a pH of 6.2 to 6.8, or a pH of 6.3 to 6.7; and preparing a conjugate by linking the linker of the mono-PEGylated immunoglobulin Fc region purified in the above-described step to a dual agonist exhibiting activity on both GLP-1 and glucagon, without being limited thereto.

In addition, in the preparation method of the present invention, (i) the mono-PEGylated immunoglobulin Fc region may be prepared by linking the linker of Formula 1 to the N-terminus of the immunoglobulin Fc region in the presence of a reducing agent at a pH of 4.0 to 8.0, a pH of 4.5 to 7.5, a pH of 5.5 to 7.5, a pH of 5.6 to 7.4, a pH of 5.7 to 7.3, or a pH of 5.8 to 7.2; and/or (ii) the conjugate may be prepared by linking the linker of the mono-PEGylated immunoglobulin Fc region to the dual agonist at a pH of 5.5 to 8.0, a pH of 6.0 to 7.5, or a pH of 6.5 to 7.5, without being limited thereto.

In addition, the step of preparing the conjugate according to the preparation method of the present invention may be performed by reacting the dual agonist in an amount equivalent to or more than an amount of the mono-PEGylated immunoglobulin Fc region, and specifically, a molar ratio of mono-PEGylated immunoglobulin Fc region: dual agonist may be from 1:1 to 1:10, from 1:1 to 1:7, from 1:1 to 1:5, or from 1:1 to 1:3, but is not limited thereto.

As used herein, the term "protein conjugate" refers to a conjugate of proteins having an increased half-life and having a structure in which the dual agonist exhibiting activity on both glucagon-like peptide-1 (GLP-1) and glucagon is linked to the immunoglobulin Fc region via the linker.

As used herein, the term "dual agonist" refers to a substance exhibiting activity on both receptors of GLP-1 and glucagon and including one of the amino acid sequences of SEQ ID NOS: 1 to 3.

The method for preparing a protein conjugate according to the present invention may be a method for preparing a conjugate in which an oxyntomodulin derivative is linked to an immunoglobulin Fc region via a linker, but is not limited thereto.

As used herein, the term "immunoglobulin Fc region" refers to a region including a heavy chain constant domain 2 (CH2) and/or a heavy chain constant domain 3 (CH3) excluding the heavy chain and light chain variable domains of the immunoglobulin. The immunoglobulin Fc region may be a component constituting a moiety of the conjugate of the present invention. Specifically, the immunoglobulin Fc region of the present invention may include, essentially consist of, or consist of an amino acid sequence of SEQ ID NO: 7, but is not limited thereto.

In the present invention, the immunoglobulin Fc region includes a particular hinge sequence at the N-terminus.

As used herein, the term "hinge sequence" refers to a site located at a heavy chain and forming a dimer of the immunoglobulin Fc region via an inter disulfide bond.

In the present invention, the hinge sequence may be mutated to have only one cysteine residue by deletion of a part of the hinge sequence including the amino acid sequence below, but is not limited thereto:

Glu-Ser-Lys-Tyr-Gly-Pro-Pro-Cys-Pro-Ser-Cys-Pro (SEQ ID NO: 4).

In view of the objects of the present invention, the hinge sequence may include only one cysteine residue as a cysteine residue located at the 8th or 11th position of the hinge sequence of SEQ ID NO: 4 is deleted. The hinge sequence of the present invention may consist of 3 to 12 amino acids including only one cysteine residue, without being limited thereto. More specifically, the hinge sequence of the present invention may have a sequence as follows: Glu-Ser-Lys-Tyr-Gly-Pro-Pro-Pro-Ser-Cys-Pro (SEQ ID NO: 8), Glu-Ser-Lys-Tyr-Gly-Pro-Pro-Cys-Pro-Ser-Pro SEQ ID NO: 9), Glu-Ser-Lys-Tyr-Gly-Pro-Pro-Cys-Pro-Ser (SEQ ID NO: 10), Glu-Ser-Lys-Tyr-Gly-Pro-Pro-Cys-Pro-Pro (SEQ ID NO: 11), Lys-Tyr-Gly-Pro-Pro-Cys-Pro-Ser (SEQ ID NO: 12), Glu-Ser-Lys-Tyr-Gly-Pro-Pro-Cys (SEQ ID NO: 13), Glu-Lys-Tyr-Gly-Pro-Pro-Cys (SEQ ID NO: 14), Glu-Ser-Pro-Ser-Cys-Pro (SEQ ID NO: 15), Glu-Pro-Ser-Cys-Pro (SEQ ID NO: 16), Pro-Ser-Cys-Pro (SEQ ID NO: 17), Glu-Ser-Lys-Tyr-Gly-Pro-Pro-Ser-Cys-Pro (SEQ ID NO: 18), Lys-Tyr-Gly-Pro-Pro-Pro-Ser-Cys-Pro (SEQ ID NO: 19), Glu-Ser-Lys-Tyr-Gly-Pro-Ser-Cys-Pro (SEQ ID NO: 20), Glu-Ser-Lys-Tyr-Gly-Pro-Pro-Cys (SEQ ID NO: 21), Lys-Tyr-Gly-Pro-Pro-Cys-Pro (SEQ ID NO: 22), Glu-Ser-Lys-Pro-Ser-Cys-Pro (SEQ ID NO: 23), Glu-Ser-Pro-Ser-Cys-Pro (SEQ ID NO: 24), or Glu-Pro-Ser-Cys (SEQ ID NO: 25). More specifically, the hinge sequence may include an amino acid sequence of SEQ ID NO: 5 (Ser-Cys-Pro) or SEQ ID NO: 6 (Pro-Ser-Cys-Pro), without being limited thereto.

The immunoglobulin Fc region of the present invention may be in the form of a dimer formed of two chain molecules of the immunoglobulin Fc region in the presence of the hinge sequence, and the protein conjugate of the present invention may be in a form in which one end of the linker is linked to one chain of the immunoglobulin Fc region as a dimer, without being limited thereto.

As used herein, the term "N-terminus" refers to an amino terminus of a protein or polypeptide and may include an amino acid residue located at the end of the amino terminus or 1, 2, 3, 4, 5, 6, 7, 8, 9, 10, or more amino acids from the end of the amino terminus. The immunoglobulin Fc region of the present invention may include the hinge sequence at the N-terminus, without being limited thereto.

Meanwhile, the immunoglobulin Fc region of the present invention may be an extended Fc region including a part of or the entirety of a heavy chain constant domain 1 (CH1) and/or a light chain constant domain 1 (CL1) excluding the heavy chain and the light chain variable domains of the immunoglobulin, as long as the immunoglobulin Fc region has substantially identical or enhanced effects compared to the native type. Also, the immunoglobulin Fc region may be a region from which a considerably long part of the amino acid sequence corresponding to the CH2 and/or CH3 is removed.

For example, the immunoglobulin Fc region of the present invention may include 1) CH1 domain, CH2 domain, CH3 domain and CH4 domain, 2) CH1 domain and CH2 domain, 3) CH1 domain and CH3 domain, 4) CH2 domain and CH3 domain, 5) a combination of one or more domains selected from CH1 domain, CH2 domain, CH3 domain, and CH4 domain and an immunoglobulin hinge region (or a part of the hinge region), or 6) a dimer of each domain of the heavy chain constant domain and the light chain constant domain. However, the present invention is not limited thereto.

Also, the immunoglobulin Fc region of the present invention includes not only a naturally occurring amino acid sequence but also a sequence derivative thereof. The amino acid sequence derivative refers to a sequence different from the naturally occurring amino acid sequence due to a deletion, insertion, non-conservative or conservative substitution, or any combination of one or more amino acids of the naturally occurring amino acid sequence.

For example, in the case of IgG Fc, amino acid residues known to be important in linkage at positions 214 to 238, 297 to 299, 318 to 322, or 327 to 331 may be used as a suitable target for modification.

Also, other various derivatives including those in which a site capable of forming a disulfide bond is deleted or certain amino acid residues are eliminated from the N-terminus of a native Fc form, or a methionine residue is added to the N-terminus of the native Fc form may be used. In addition, to remove effector functions, a complement binding site, such as a C1q binding site, may be deleted, and an antibody dependent cell mediated cytotoxicity (ADCC) site may be deleted. Techniques of preparing such sequence derivatives of the immunoglobulin Fc region are disclosed in International Patent Publication Nos. WO 97/34631 and WO 96/32478.

Amino acid exchanges in proteins and peptides, which do not generally alter the activity of molecules, are known in the art (H. Neurath, R. L. Hill, *The Proteins*, Academic Press, New York, 1979). The most commonly occurring exchanges of amino acid residues are exchanges between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, LeuNal, Ala/Glu, and Asp/Gly. If required, the Fc region may be modified by phosphorylation, sulfation, acrylation, glycosylation, methylation, farnesylation, acetylation, and amidation.

The above-described sequence derivatives of the immunoglobulin Fc region are derivatives that have a biological activity equivalent to the immunoglobulin Fc region of the present invention or improved structural stability against heat, pH, or the like.

In addition, these immunoglobulin Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. In this regard, they may be obtained from a native immunoglobulin by isolating whole immunoglobulins from living humans or animals and treating them with a protease. Papain digests the native immunoglobulin into Fab and Fc regions and pepsin digests the native immunoglobulin into pF'c and $F(ab)_2$ fragments. These fragments may be subjected to size-exclusion chromatography to isolate Fc or pF'c. In a more specific embodiment, a human-derived immunoglobulin Fc region is a recombinant immunoglobulin Fc region obtained from a microorganism.

In addition, the immunoglobulin Fc region may have natural glycans or increased or decreased glycans compared to the natural type, or be in a deglycosylated form. The increase, decrease, or removal of glycans of the immunoglobulin Fc may be achieved by any methods commonly used in the art such as a chemical method, an enzymatic method, and a genetic engineering method using a microorganism. In this regard, the immunoglobulin Fc region obtained by removing glycans shows a significant decrease in binding affinity to a complement c1q and a decrease in or loss of antibody-dependent cytotoxicity or complement-dependent cytotoxicity, and thus unnecessary immune responses are not induced thereby in living organisms. Based thereon, a deglycosylated or aglycosylated immunoglobulin Fc region may be more suitable as a drug carrier in view of the objects of the present invention.

As used herein, the term "deglycosylation" refers to an Fc region from which glycan is removed using an enzyme and the term "aglycosylation" refers to an Fc region that is not glycosylated and produced in prokaryotes, more specifically, *E. coli*.

Meanwhile, the immunoglobulin Fc region may be derived from humans or animals such as cows, goats, swine, mice, rabbits, hamsters, rats, or guinea pigs. In a more specific embodiment, the immunoglobulin Fc region may be derived from humans.

In addition, the immunoglobulin Fc region may be derived from IgG, IgA, IgD, IgE, or IgM, or any combination or hybrid thereof. In a more specific embodiment, the immunoglobulin Fc region is derived from IgG or IgM which are the most abundant proteins in human blood, and in an even more specific embodiment, it is derived from IgG known to enhance the half-lives of ligand binding proteins. In a yet even more specific embodiment, the immunoglobulin Fc region is an IgG4 Fc region, and in the most specific embodiment, the immunoglobulin Fc region is an aglycosylated Fc region derived from human IgG4, without being limited thereto.

Meanwhile, as used herein, the term "combination" related to the immunoglobulin Fc region refers to formation of a linkage between a polypeptide encoding a single-chain immunoglobulin Fc region of the same origin and a single-chain polypeptide of a different origin when a dimer or a multimer is formed. That is, a dimer or multimer may be prepared using two or more Fc fragments selected from the group consisting of IgG Fc, IgA Fc, IgM Fc, IgD Fc, and IgE Fc fragments.

As used herein, the term "hybrid" means that sequences corresponding to two or more immunoglobulin constant domains of different origins are present in a single-chain of an immunoglobulin constant domain. In the present invention, various hybrid forms are possible. That is, a domain hybrid may be composed of 1 to 4 domains selected from the group consisting of CH1, CH2, CH3, and CH4 of IgG Fc, IgM Fc, IgA Fc, IgE Fc, and IgD Fc and may further include a hinge region.

As used herein, the term "linker" refers to a moiety linking a protein (e.g., dual agonist) to the immunoglobulin Fc region in the protein conjugate, and the linker may be a peptidyl linker or a non-peptidyl linker.

Specifically, the linker may be represented by Formula 1 below, without being limited thereto:

$$CHO\text{-}L1\text{-}(OCH_2CH_2)_nO\text{-}L2\text{-}R \quad \text{[Formula 1]}$$

In Formula 1 above,

L1 is a straight- or branched-chain $C_1$-$C_6$ alkylene;

L2 is -a1-CONH—, -a1-NHCO—, -a1-NHCO-a2-, —COO—, -b1-COO—, -COO-b2-, or -b1-COO-b2-, and a1, a2, b1, and b2 are each independently a straight- or branched-chain $C_1$-$C_6$ alkylene;

n is from 1 to 3000, from 10 to 2000, from 50 to 1000, from 100 to 700, from 150 to 300, or from 200 to 250;

R is 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, or p-nitrophenyl carbonate, and the linker includes polyethylene glycol and has particular chemical structures at both ends of polyethylene glycol, without being limited thereto.

Specifically, in Formula 1 above, L1 is straight-chain or branched $C_1$-$C_6$ alkylene; L2 is -a1-NHCO— or -a1-NHCO-a2-, a1and a2 are each independently straight- or branched-chain $C_1$-$C_6$ alkylene; n is from 200 to 250; R is maleimide, and the linker has a size of 1 kDa to 200 kDa, 1 kDa to 150 kDa, 1 kDa to 100 kDa, 1 kDa to 50 kDa, or 1 kDa to 10 kDa, without being limited thereto.

In addition, the linker may have a structure of Formula 2 below, but is not limited thereto.

[Formula 2]

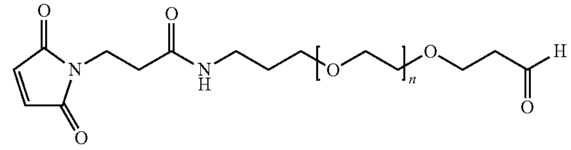

In Formula 2 above, n may be from 1 to 3000, from 10 to 2000, from 50 to 1000, from 100 to 700, from 150 to 300, or from 200 to 250.

One end of the linker may be linked to the immunoglobulin Fc region, specifically, the N-terminus of the immunoglobulin Fc region, more specifically, the hinge sequence located at the N-terminus of the immunoglobulin Fc region, specifically, a proline residue of the hinge sequence, but is not limited thereto.

As used herein, the term "mono-PEGylated immunoglobulin Fc region" refers to an intermediate substance that is produced in the middle of the method for preparing the protein conjugate according to the present invention in which one linker including one polyethylene glycol is linked to the immunoglobulin Fc region. The linkage between the linker and the immunoglobulin Fc region may be formed by a covalent or non-covalent bond between one end of the linker and the N-terminus of the immunoglobulin Fc region, but a position or a method for the linkage is not particularly limited. Specifically, the mono-PEGylated immunoglobulin Fc region may be prepared by linking a proline at the N-terminus of the immunoglobulin Fc region to a —CHO group of the linker, without being limited thereto.

The mono-PEGylated immunoglobulin Fc region may have a structure of Formula 3 below, but is not limited thereto.

[Formula 3]

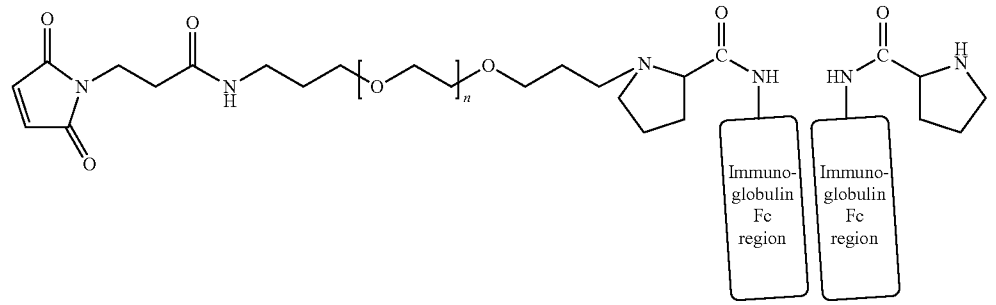

In Formula 3 above, n may be from 1 to 3000, from 10 to 2000, from 50 to 1000, from 100 to 700, from 150 to 300, or from 200 to 250; and the immunoglobulin Fc region may be an immunoglobulin Fc chain in a monomer form.

The preparation method of the present invention may be performed by linking the dual agonist to one end of the mono-PEGylated immunoglobulin Fc region having the structure of Formula 3, without being limited thereto.

In addition, the other end of the linker which is not linked to the immunoglobulin Fc region may be linked to the dual agonist, specifically, a -SH group or an amino acid containing a —SH group, or a cysteine of the dual agonist, without being limited thereto.

When the protein conjugate is prepared according to the preparation method of the present invention in which the mono-PEGylated immunoglobulin Fc region is prepared first and linked to the dual agonist, it was confirmed that the purity of the final conjugate may be maintained with an increased yield compared to the conventional preparation method even though the ultrafiltration/diafiltration and hydrophobic interaction chromatography processes are omitted and only the final purification process (e.g., hydrophobic interaction chromatography once) is performed in the preparation method according to the present invention.

Another aspect of the present invention provides a protein conjugate prepared by way of the above-described method.

The protein conjugate prepared according to the preparation method of the present invention exhibits an increased half-life compared to the dual agonist not linked to the linker or the immunoglobulin Fc region, thereby have beneficial effects on manufacturing pharmaceuticals.

The protein conjugate including the dual agonist may be used for prevention, treatment, or alleviation of obesity, metabolic disease, hyperlipidemia, and the like.

Hereinafter, the present invention will be described in more detail with reference to the following examples. However, the following examples are merely presented to exemplify the present invention, and the scope of the present invention is not limited thereto.

COMPARATIVE EXAMPLE: PREPARATION OF CONJUGATE BY LINKAGE OF PEGYLATED OXYNTOMODULIN DERIVATIVE TO IMMUNOGLOBULIN FC REGION

A PEGylated oxyntomodulin derivative was linked to an immunoglobulin Fc region to prepare a long-acting conjugate.

In order to PEGylate an oxyntomodulin derivative (SEQ ID NO: 1) at a cysteine residue (—SH group), the oxyntomodulin derivative was reacted with a linker containing PEG (Formula 2, 10 kDa, NOF corporation) for about 1 hour in a molar ratio (oxyntomodulin derivative:PEG-containing linker) of 1:1 to 1:1.3 with an oxyntomodulin derivative concentration of about 3 g/L. Specifically, the reaction was performed in a Tris buffer containing isopropanol (6° C.±4° C.). In order to obtain a mono-PEGylated oxyntomodulin derivative, the reaction solution was diluted with an equilibrium buffer including sodium citrate and ethanol to a total volume of 20 times and purified. In this regard, the mono-PEGylated oxyntomodulin derivative was purified using an SP High Performance column (GE Healthcare, cation-exchange chromatography) using a solution including sodium citrate and ethanol and a potassium chloride concentration gradient. After the purified solution of the PEGylated oxyntomodulin derivative was diluted with water, the buffer solution was replaced with a 0.1 M potassium phosphate solution through ultrafiltration/diafiltration (UF/DF), followed by concentration to recover a resultant with a final concentration of about 3 g/L or more.

The mono-PEGylated oxyntomodulin derivative prepared as described above was linked to an immunoglobulin Fc region to prepare a long-acting conjugate as follows.

In order to link an aldehyde group of the mono-PEGylated oxyntomodulin derivative to an amino terminus of an immunoglobulin Fc region, the mono-PEGylated oxyntomodulin derivative was reacted with the immunoglobulin Fc region in a molar ratio of 1:2.5 to 1:5 at a temperature of 6° C.±4° C. for about 12 to 16 hours such that a total protein concentration (oxyntomodulin derivative and immunoglobulin Fc region) was about 35 g/L.

In order to isolate and remove unreacted immunoglobulin Fc regions after the reaction for linkage, the reaction solution was purified using a Butyl 4 Fast Flow column (GE Healthcare, hydrophobic interaction chromatography). In this case, a Tris buffer and sodium chloride were added to the reaction solution, and the reaction solution was purified using a solution including a Bis-Tris and a sodium chloride concentration gradient.

Thereafter, using a Source 15ISO column (GE Healthcare), hydrophobic interaction chromatography was performed. By-products were eliminated by this process, and an immunoglobulin Fc region—PEG-containing linker—oxyntomodulin derivative conjugate was obtained. In this case, purification was performed using a buffer including sodium citrate and an ammonium sulfate concentration gradient. The present inventors have developed a process capable of efficiently producing the conjugate with a high purity by omitting the membrane filtration process and the purification process (hydrophobic interaction chromatography, Butyl 4 Fast Flow) from the process of manufacturing the conjugate according to the above-described Comparative Example as follows.

EXAMPLE 1: PREPARATION OF MONO-PEGYLATED IMMUNOGLOBULIN FC REGION

Example 1-1. Preparation of Mono-PEGylated Immunoglobulin Fc Region

In order to PEGylate the N-terminus of an immunoglobulin Fc region (49.8 kDa, SEQ ID NO: 7) having a hinge region with a Pro-Ser-Cys-Pro sequence at the N-terminus, the immunoglobulin Fc region was reacted with a linker containing PEG (structure of Formula 2, 10 kDa) in a molar ratio (immunoglobulin Fc region:PEG-containing linker) of 1:1 with a concentration of 50 g/L of the immunoglobulin Fc region at 6° C.±4° C. for about 4 hours.

[Formula 2]

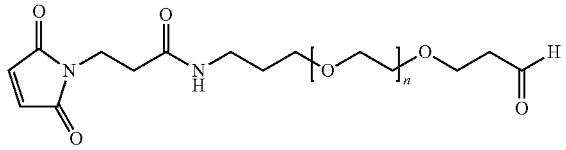

Specifically, the reaction was performed in a composition including a 5 mM Bis-Tris buffer (pH 6.5) and potassium phosphate, and 10 mM $NaCNBH_3$ (sodium cyanoborohydride) was added thereto as a reducing agent. In order to obtain a mono-PEGylated immunoglobulin Fc region, the reaction solution was diluted with the Bis-Tris buffer and purified.

Unlike the preparation method of the above-described Comparative Example in which the mono-PEGylated oxyntomodulin was purified by cation-exchange chromatography, the mono-PEGylated immunoglobulin Fc region was purified using a CaptoQ ImpRes column (GE Healthcare, anion-exchange chromatography) using a Bis-Tris buffer and a sodium chloride concentration gradient.

Example 1-2. Analysis of Structure of Mono-PEGylated Immunoglobulin Fc Region The mono-PEGylated immunoglobulin Fc region prepared in Example 1-1 was structurally analyzed by MALDI-TOF and Peptide mapping. As a result of MALDI-TOF, the resultant was identical to an expected molecular weight of the mono-PEGylated immunoglobulin Fc region (FIG. 1), and as a result of Peptide mapping, it was confirmed that over 90% of PEG was PEGylated at the N-terminus of the immunoglobulin Fc region.

Meanwhile, as a result of analyzing the mono-PEGylated immunoglobulin Fc region (Formula 3) prepared in Example 1-1 above using SE-HPLC, RP-HPLC, and IE-HPLC assays, the purity was confirmed to be 90% or more in SE-HPLC, 90% or more in RP-HPLC, and 80% or more in IE-HPLC.

[Formula 3]

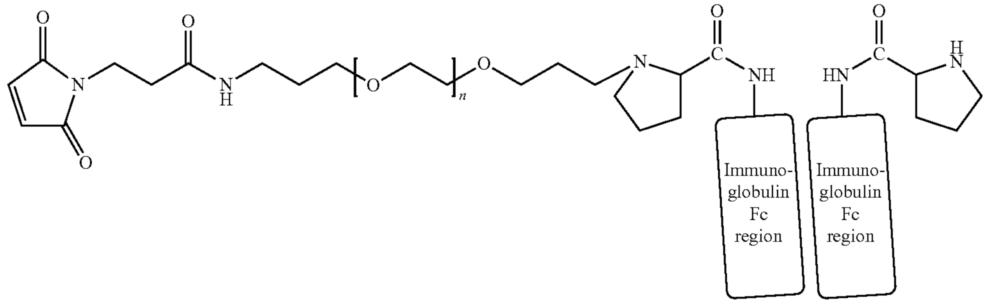

EXAMPLE 2: PREPARATION OF CONJUGATE BY LINKAGE OF PEGYLATED IMMUNOGLOBULIN FC REGION TO OXYNTOMODULIN DERIVATIVE

A long-acting conjugate was prepared as follows by linking the mono-PEGylated immunoglobulin Fc region prepared in Example 1-1 to an oxyntomodulin derivative.

Unlike the preparation method of Comparative Example where the PEGylated peptide was purified by cation-exchange chromatography and then subjected to buffer exchange and concentration by ultrafiltration/diafiltration (UF/DF), the mono-PEGylated immunoglobulin Fc region was reacted with the oxyntomodulin derivative via peptide conjugation without performing ultrafiltration/diafiltration. The long-acting conjugate prepared as described above had high purity, and thus one of the two performances of hydrophobic interaction chromatography could be omitted unlike the preparation method according to Comparative Example.

Specifically, the long-acting conjugate (immunoglobulin Fc region—PEG-containing linker-oxyntomodulin derivative) was prepared via peptide conjugation of the oxyntomodulin derivative (SEQ ID NO: 1), which is a dual agonist for GLP-1 and glucagon, after anion-exchange chromatography of Example 1-1 without performing ultrafiltration/diafiltration.

[SEQ ID NO: 1]

HXQGTFTSDYSKYLD(EKRAK)EFVQWLMNTC

X = 2-aminoisobutyric acid
Glu16 and Lys20 linked by Lactam ring

In this regard, in order to link a maleimide reactive group at one terminus of PEG of the mono-PEGylated immunoglobulin Fc region to cysteine of the oxyntomodulin derivative, the mono-PEGylated immunoglobulin Fc region was reacted with the oxyntomodulin derivative in a molar ratio of 1:1 with an oxyntomodulin derivative protein concentration of 0.2 g/L at 6° C.±4° C. for about 2 hours. The reaction solution was maintained in a Tris-Cl buffer (6° C.±4° C.) including isopropanol. As a result of analyzing the resultant after reaction using SE-HPLC, RP-HPLC, and IE-HPLC assays, the purity of the immunoglobulin Fc region—PEG-containing linker—oxyntomodulin derivative conjugate (Formula 4) was confirmed to be 90% or more in SE-HPLC, 80% or more in RP-HPLC, and 80% or more in IE-HPLC.

Thereafter, the resultant of the reaction was subjected to hydrophobic interaction chromatography once using a Source 15ISO column (GE Healthcare). By-products were eliminated by this process, and the immunoglobulin Fc region—PEG-containing linker-oxyntomodulin derivative conjugate was obtained. In this case, purification was performed using a buffer including sodium citrate and an ammonium sulfate concentration gradient. It was confirmed that a yield obtained herein was increased by about twice or more compared to a yield of Comparative Example with the same amount of the oxyntomodulin derivative.

The eluted immunoglobulin Fc region—PEG-containing linker—oxyntomodulin derivative conjugate (Formula 4) was analyzed by MALDI-TOF, SE-HPLC, RP-HPLC, and IE-HPLC assays. It was confirmed that the resultant was identical to an expected molecular weight of the immunoglobulin Fc region—PEG-containing linker—oxyntomodulin derivative conjugate based on the analysis results of MALDI-TOF. Also, high purity was confirmed since the purity was 90% or more in SE-HPLC, 90% or more in RP-HPLC, and 90% or more in IE-HPLC.

[Formula 4]

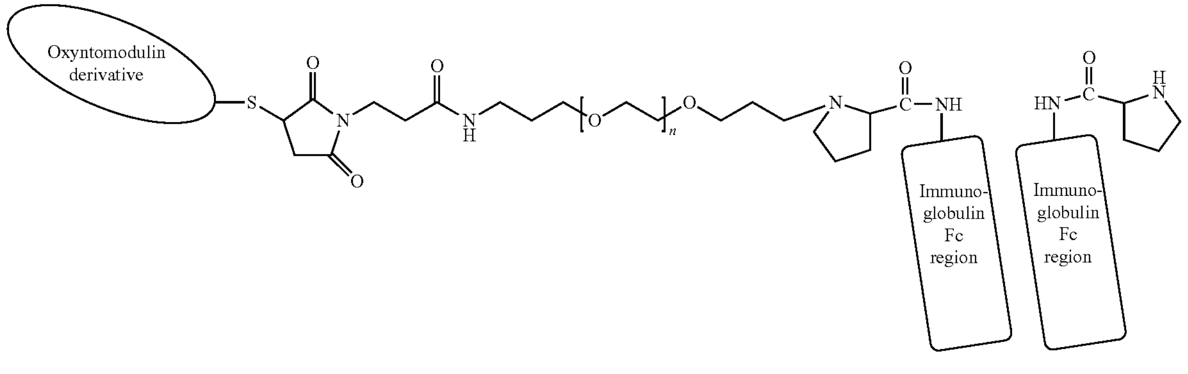

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the present invention.

The invention claimed is:

1. A method for preparing a protein conjugate, the method comprising preparing a conjugate by linking a mono-PEGylated immunoglobulin Fc region, which is prepared by linking a linker of Formula 1 below to the N-terminus of an immunoglobulin Fc region comprising a hinge sequence, to C-terminal cysteine of a glucagon-like peptide-1 (GLP-1) receptor/glucagon receptor dual agonist comprising the amino acid sequence set forth in SEQ ID NO: 1 or 2:

$CHO-L1-(OCH_2CH_2)_nO-L2-R$ [Formula 1]

wherein in Formula 1:

L1 is a straight- or branched-chain $C_1$-$C_6$ alkylene;

L2 is -a1-CONH-, -a1-NHCO-, -a1-NHCO-a2-, -COO-, -b1-COO-, -COO-b2-, or -b1-COO-b2-, and a1, a2, b1, and b2 are each independently a straight- or branched-chain $C_1$-$C_6$ alkylene;

n is from 10 to 2,400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

2. The method according to claim 1, wherein the mono-PEGylated immunoglobulin Fc region is prepared by linking the linker of Formula 1 above to the N-terminus of the immunoglobulin Fc region at a pH of 4.0 to 8.0 in the presence of a reducing agent.

3. The method according to claim 1, wherein the conjugate is prepared by linking the linker of the mono-PEGylated immunoglobulin Fc region to the C-terminal cysteine of the GLP-1 receptor/glucagon receptor dual agonist at a pH of 5.5 to 8.0.

4. The method according to claim 1, wherein the preparing of the conjugate comprises reacting the mono-PEGylated immunoglobulin Fc region with the GLP-1 receptor/glucagon receptor dual agonist in a molar ratio of 1:1 to 1:3.

5. The method according to claim 1, wherein the method comprises:

preparing a mono-PEGylated immunoglobulin Fc region by linking a linker of Formula 1 above to the N-terminus of an immunoglobulin Fc region;

purifying the mono-PEGylated immunoglobulin Fc region prepared in the step above by anion-exchange chromatography in a buffer solution with a pH of 6.0 to 8.5; and preparing a conjugate by linking the linker of the mono-PEGylated immunoglobulin Fc region purified in the step above to the GLP-1 receptor/glucagon receptor dual agonist.

6. The method according to claim 1, wherein the method is performed without ultrafiltration/diafiltration after preparing the mono-PEGylated immunoglobulin Fc region.

7. The method according to claim 1, further comprising purifying the conjugate by performing hydrophobic interaction chromatography once.

8. The method according to claim 1, wherein in Formula 1 above, L1 is a straight- or branched-chain $C_1$-$C_6$ alkylene; L2 is -a1-NHCO- or -a1-NHCO-a2-; a1 and a2 are each independently a straight- or branched-chain $C_1$-$C_6$ alkylene; n is from 200 to 250; and R is maleimide.

9. The method according to claim 1, wherein the linker has comprises a structure of Formula 2 below:

[Formula 2]

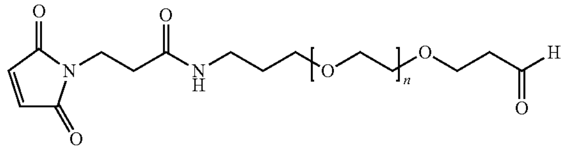

wherein in Formula 2, n is from 200 to 250.

10. The method according to claim 1, wherein the linker has a size of 1 kDa to 100 kDa.

11. The method according to claim 1, wherein the mono-PEGylated immunoglobulin Fc region comprises a structure of Formula 3 below:

[Formula 3]

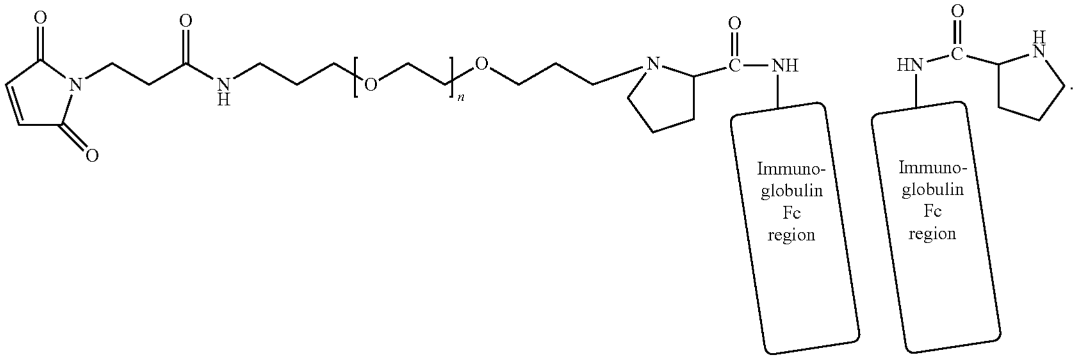

12. The method according to claim 1, wherein the immunoglobulin Fc region comprises the amino acid sequence of SEQ ID NO: 7.

13. A protein conjugate comprising a mono-PEGylated immunoglobulin Fc region linked to the C-terminal cysteine of a GLP-1 receptor/glucagon receptor dual agonist comprising the amino acid sequence set forth in SEQ ID NO: 1 or 2 prepared according to the method of claim 1.

* * * * *